Figure 1:
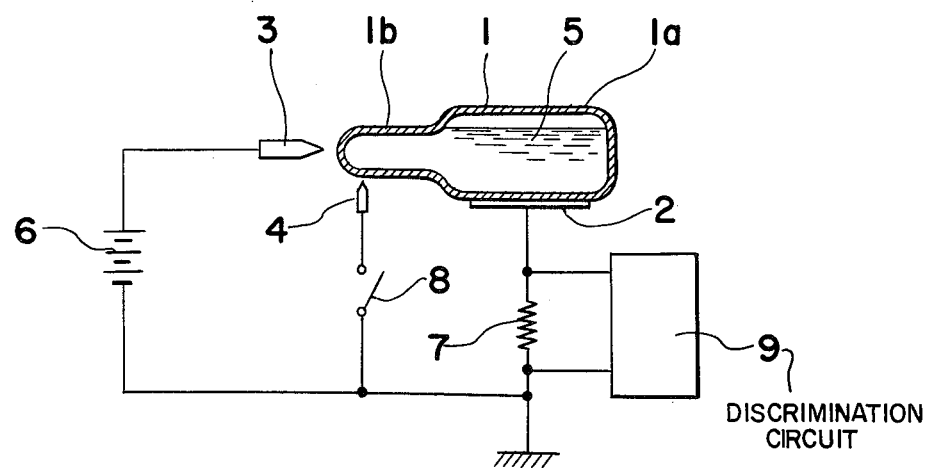

United States Patent [19]

Nagamatsu et al.

[11] 4,125,805

[45] Nov. 14, 1978

[54] METHOD AND APPARATUS FOR DEFECT INSPECTION OF LIQUID-FILLED INSULATING CONTAINER

[75] Inventors: Kazuo Nagamatsu, Takarazuka; Tadao Yasuhara, Takatsuki; Masakazu Oi, Osaka; Hideaki Maeda, Takarazuka, all of Japan

[73] Assignee: Takeda Chemical Industries, Ltd., Osaka, Japan

[21] Appl. No.: 785,601

[22] Filed: Apr. 7, 1977

[30] Foreign Application Priority Data

Jul. 15, 1976 [JP]  Japan .................................. 51-84805
Dec. 18, 1976 [JP]  Japan .................................. 51-152620

[51] Int. Cl.$^2$ ...................... G01R 31/12; G01N 27/60
[52] U.S. Cl. ..................................... 324/54; 324/71 R
[58] Field of Search ................... 324/54, 71 R, 32, 72

[56] References Cited

U.S. PATENT DOCUMENTS

| | | | |
|---|---|---|---|
| 2,701,336 | 2/1955 | Anderson | 324/54 |
| 3,234,462 | 2/1966 | Holdsworth | 324/32 X |
| 3,321,703 | 5/1967 | Tyszewicz | 324/54 |
| 3,358,378 | 12/1967 | Downs | 324/32 X |
| 3,443,224 | 5/1969 | Kramer et al. | 324/32 X |
| 3,611,122 | 10/1971 | Pahl | 324/54 |
| 3,639,831 | 2/1972 | Cushman | 324/54 X |
| 3,866,114 | 2/1975 | Johnston | 324/54 X |
| 3,919,635 | 11/1975 | Bowen et al. | 324/54 |

*Primary Examiner*—Gerard R. Strecker
*Attorney, Agent, or Firm*—Wenderoth, Lind & Ponack

[57] ABSTRACT

The present invention is a defect inspection method and apparatus for electrically inspecting for the presence of defects in sealed containers of insulating material containing electrically conductive electrolyte or nonelectrolyte fluids, in which the container to be inspected is charged by a high DC voltage to detect the charging current developed and the current neutralizing the charging current for detecting the presence of faults in the container through the magnitudes and the shapes of these currents which are compared with reference values.

35 Claims, 19 Drawing Figures

METHOD AND APPARATUS FOR DEFECT INSPECTION OF LIQUID-FILLED INSULATING CONTAINER

The present invention relates to a defect inspection apparatus and more particularly, to a method of electrically inspecting for the presence of faulty sealed spots such as pin-holes and cracks in a sealed container of insulating material containing an electrically conductive electrolyte or nonelectrolyte fluid, for example, an ampoule or phial containing medicinal fluid, and an apparatus.

In general, inspection of the defects of sealed containers, for example ampoules of glass material containing sterilized medicinal fluids for preservation of such fluids for a long period of time constitutes an important process in the manufacturing of such sealed containers, since, if defects such as pin holes, cracks and the like are present in these sealed containers, various germs or bacteria may enter the containers together with atmospheric air through such pin holes or cracks, or the medicinal fluids contained in the sealed containers may exude or ooze out of the containers therethrough, thus making it impossible to use the medicinal fluids with safety.

Conventionally, there has been proposed one method of electrically inspecting for the presence of pin holes, cracks and the like in sealed glass containers such as ampoules of the above described kind containing electrically conductive fluids, for example, by Japanese Patent laid-open publication Tokukaisho No. 45250/48, in which the glass container is passed between electrodes charged with a high DC voltage, with the voltage having a value that will not develop a spark discharge when the glass container is free from defects, but will produce an electric arc in the presence of pin holes or cracks in the glass container, while the spark discharge current generated through the glass container by the voltage is detected for testing the same glass container for the above described defects.

In the prior art inspecting method as described above, one of the electrodes of the high voltage DC source is made to contact the glass container, while a spark gap is provided between the other of the electrodes and the portion of the glass container to be inspected so as to detect faulty sealed spots of the glass container where the fluid contained therein may exude onto the surface of the glass container by the presence of an abnormal rise in the spark discharge current developed at the spark gap. The above described conventional inspecting method, however, has a disadvantage, since the spark discharge current developed at the spark gap on which the fault detection is based is very unstable. Considerable time is required before the predetermined spark discharge takes place especially during the initial stage of the inspection. In some cases, the spark discharge is not developed even when pin holes in the order of several tens of microns in size are present in the glass container, thus resulting in failure to detect such faults. Thus it is difficult to effect fault detection with high accuracy. In order to improve the testing accuracy to overcome the above described inconveniences, the high DC voltage may be raised to such an extent that the spark discharge current is positively generated at the spark gap. In this case, however, since the energy of the spark discharge current is abnormally increased even if the spark discharge is produced without fail, there is a possibility that the glass container itself will be destroyed thereby. Furthermore, when the spark discharge current is increased as a whole, the magnitude of the spark discharge current developed according to the presence of the pin holes in the glass container tends to be erroneously detected. Moreover, in the conventional method as described above, the pin holes or the like can not be detected if nonelectrolyte fluids are contained in the glass container due to the insufficient testing accuracy.

Accordingly, an essential object of the present invention is to provide a method of electrically inspecting for the presence of defects in sealed containers and an apparatus employed therefor which accurately detect faulty sealed spots of containers of insulating material such as ampoules, phials, milk bottles, tetrapacks or paper containers, bottles, etc., made of glass, plastics, rubber or the like containing therein electrically conductive electrolyte or nonelectrolyte fluids, for example, water, water solutions, distilled water and the like having an electrical conductivity under 10 M$\Omega$-cm, with substantial elimination of the disadvantages inherent in the conventional methods and apparatuses of the kind.

Another important object of the present invention is to provide a method of electrically inspecting for the presence of defects in sealed containers as described above in which a container to be inspected is charged by a high DC voltage from a high voltage DC source to detect the charging current developed thereby and the current neutralizing the charging current for detecting the presence of faults in the container through the magnitudes and the shapes of these currents which are compared with reference values, without employing spark a discharge current developed in the spark gap between an electrode of a high voltage AC source and the portions of the container to be tested as in the conventional methods.

A further object of the present invention is to provide a defect inspecting apparatus of the above described type which is simple in construction and stable in function with high reliability, and can be manufactured at low cost.

In accomplishing these and other objects, according to the present invention, measurement of the spark discharge current generated in the spark gap between the electrode of the high voltage AC source and the portions of the glass container to be inspected as in the conventional arrangement is replaced by charging the container to be tested by a high DC voltage for detecting the charging current and current neutralizing said charging current so as to detect the presence of faults in the container through the magnitudes and the shapes of the charging current and neutralizing current which are compared with reference values. Since in the case where the fluid is leaking through the faulty sealed portions such as pin holes present in the container the charging current has an abnormal value as compared with the neutralizing current in the case where the container is free from such defects, any small faults in the container can be positively detected with accuracy. More specifically, in the arrangement of the present invention, a first of the electrode members is disposed to confront, through a predetermined space of less than approximately 200 mm, one end of the portion to be tested of the sealed container of insulating material containing fluid therein, while a second of the electrode members is made to contact the other end of the container, with a high voltage DC source in the range of approximately 0.1 to 10 KV/mm between two electrode members. An auxiliary electrode member having the same polarity as the second of the electrode members is disposed in the vicinity of the portion to be tested of the container together with switching means for opening and closing the energizing circuit for said auxiliary electrode, with a detecting means for detecting variations of the charge at the closing or opening of this switching means being further provided. In order to detect faults in the container, the switching means described above is closed after having charged the portion to be tested of the container through the first and second electrode members for causing the high DC voltage at the electrode members to be spark-discharged to the above auxiliary electrode member so as to neutralize the charging of the container and also to detect power variations at this time by the above described detecting means. Subsequently, the above portion to be tested of the container is again charged by opening the switching means for detecting charge variations at this time by the detecting means. If the detected value is abnormal or larger than a predetermined high standard value, the presence of defects such as pin holes and cracks in the container is identified; while the absence of fluid in the container is detected, if the detected value is smaller than another predetermined low standard value, thus an improved method for electrically inspecting for the presence of defects in sealed containers of insulating material and an apparatus therefor are advantageously presented. It is to be noted here that, in the arrangement of the invention as described above, various parts of the containers may serially be inspected, if the number of the above described auxiliary electrode members is increased, and that a part of the alternating current converted into a DC component may be employed as the DC high voltage source.

Figure 2:
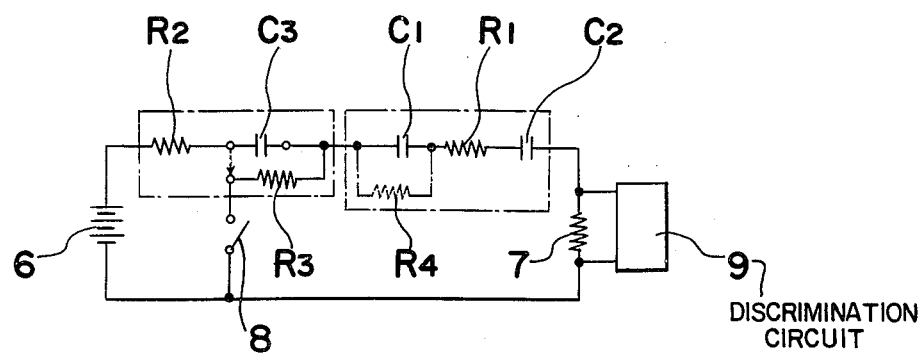
Figure 3:
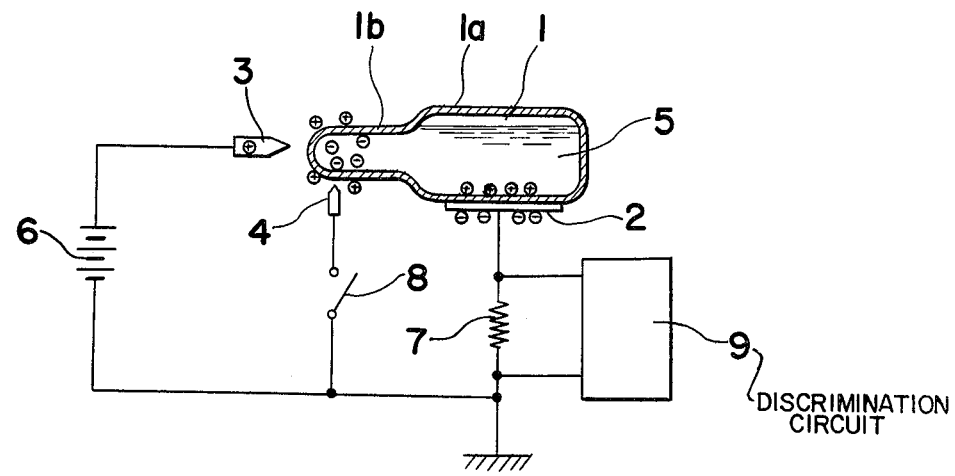
Figure 3:
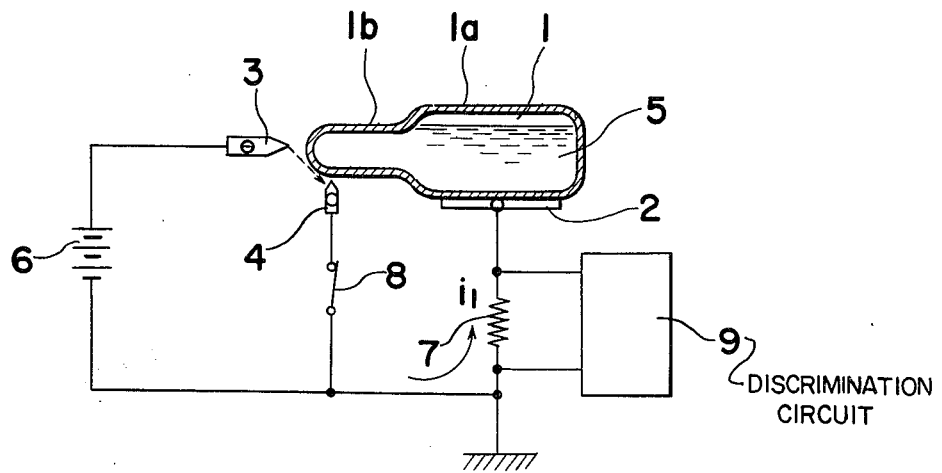
Figure 3:
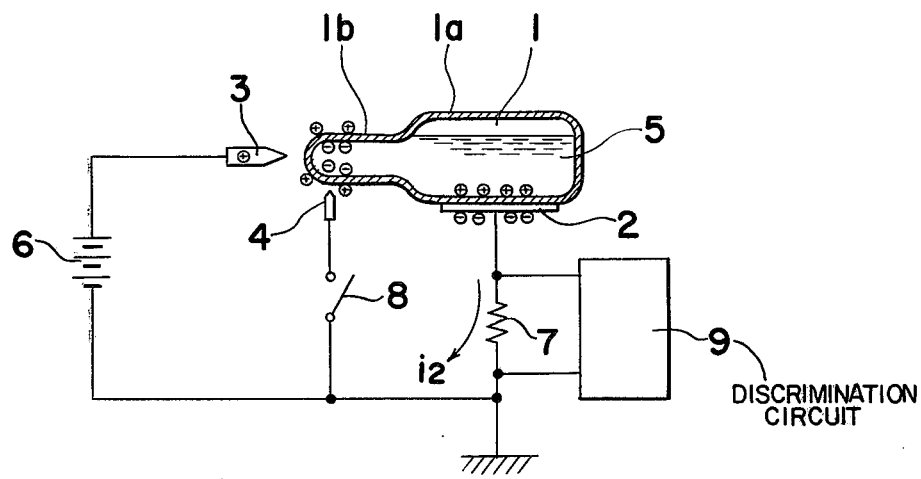
Figure 3:
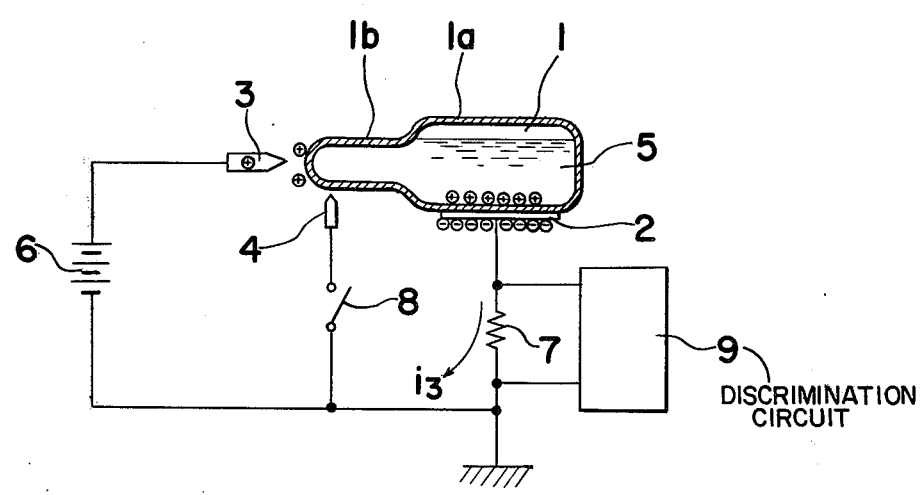
Figure 3:
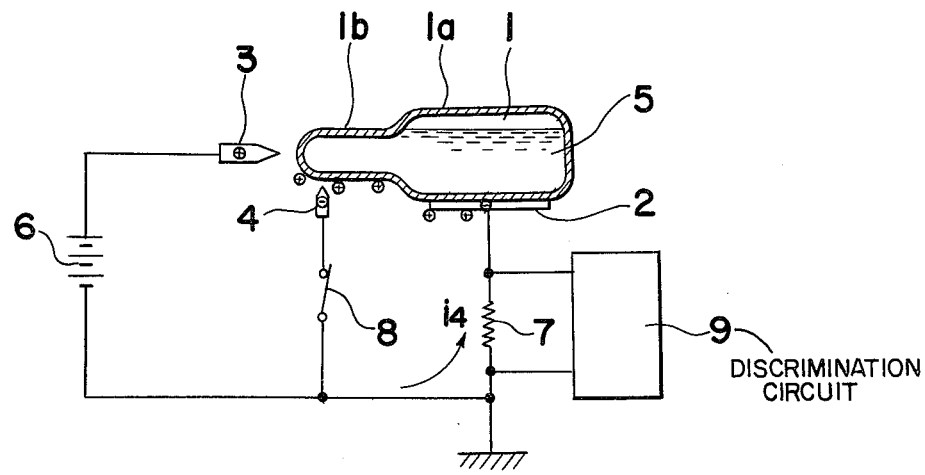
Figure 3:
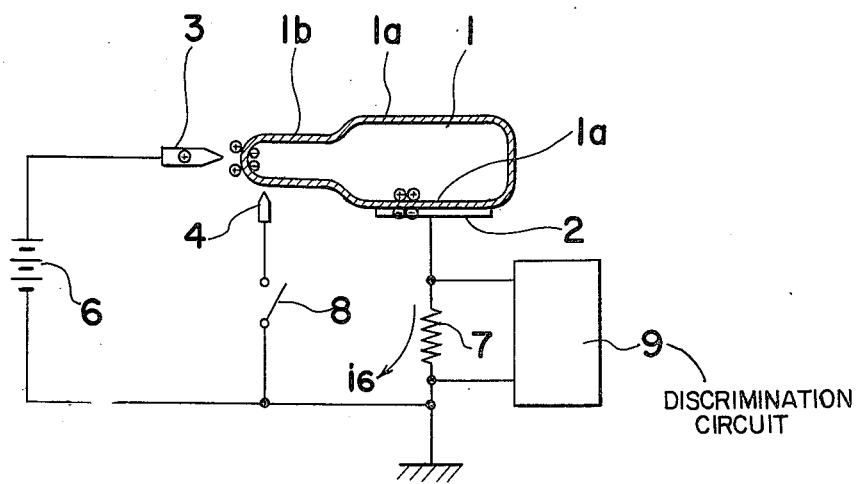
Figure 4:
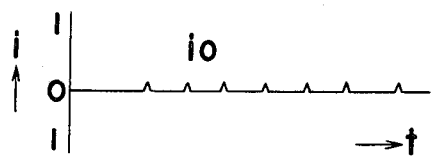
Figure 4:
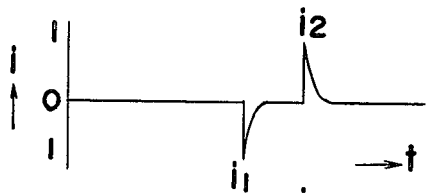
Figure 4:
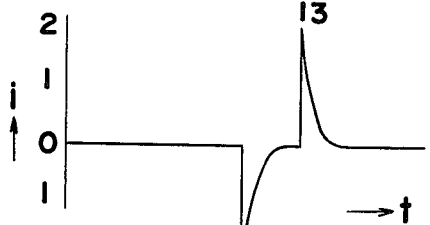
Figure 4:
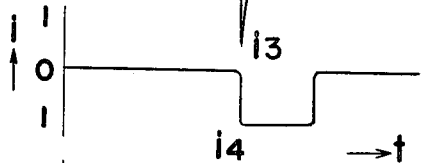
Figure 4:
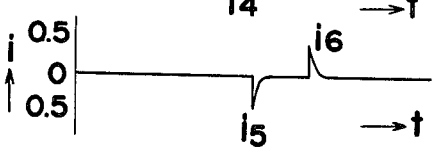
Figure 5:
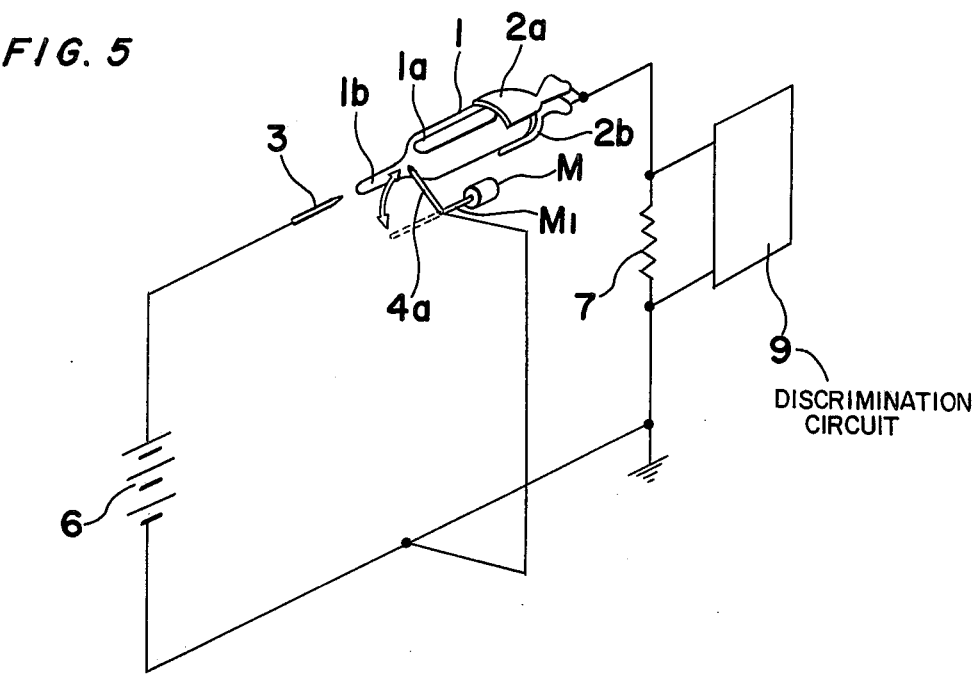
Figure 6:
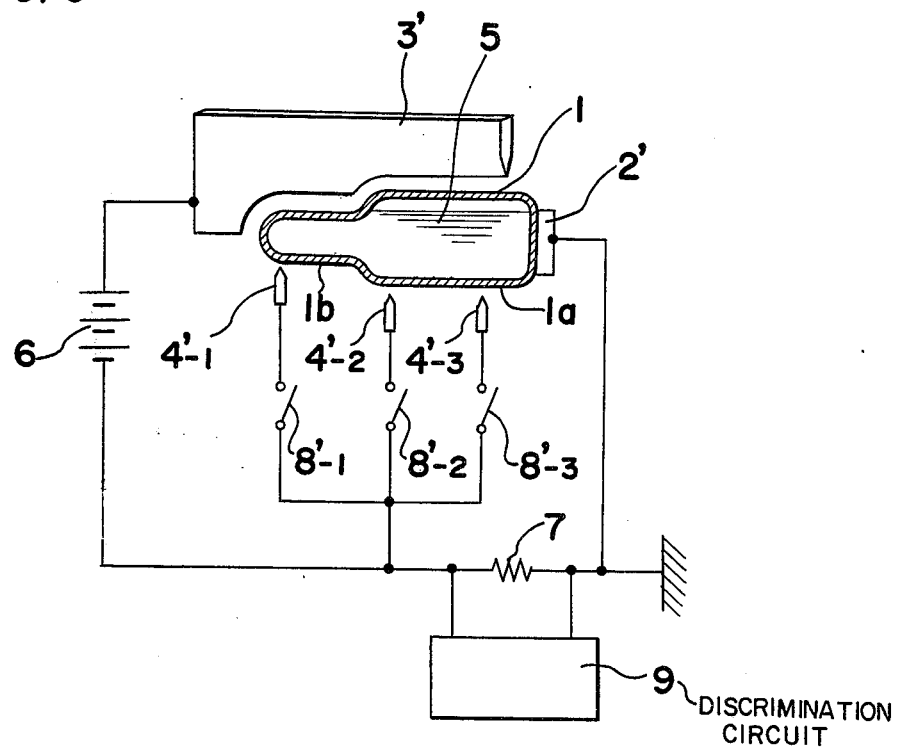
Figure 7:
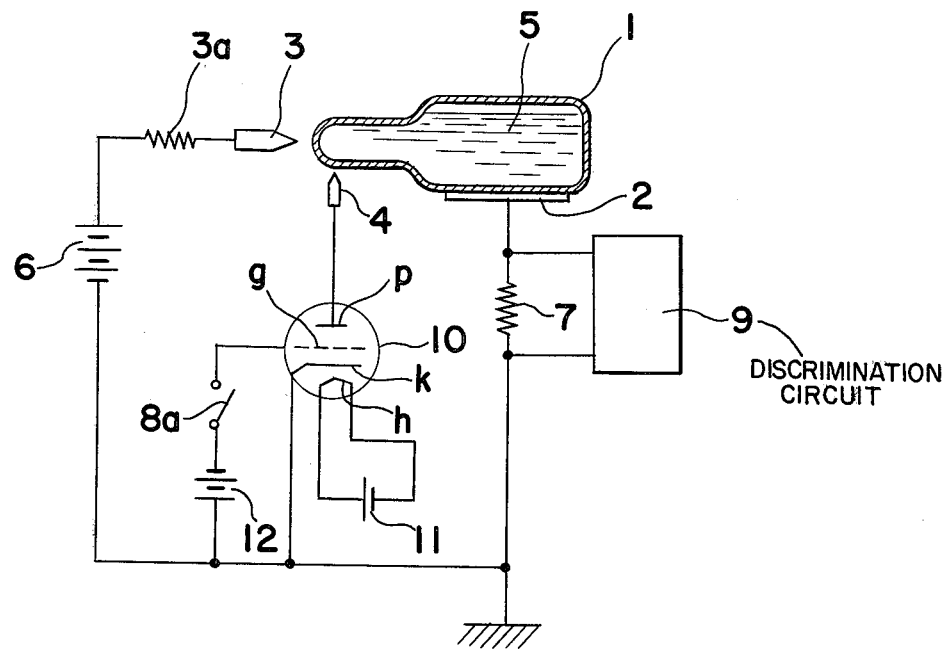
Figure 8:
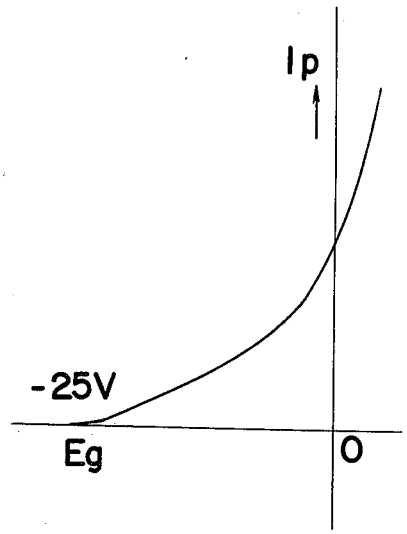
Figure 9:
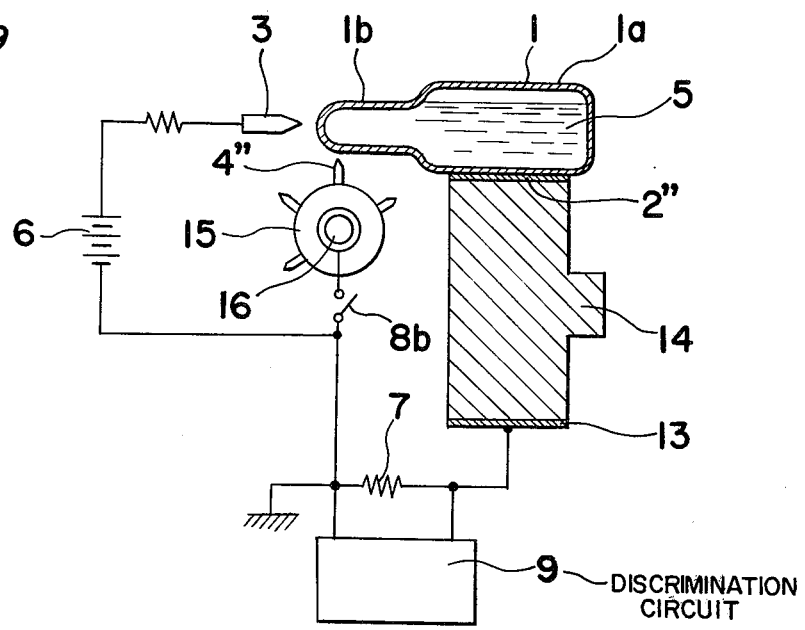
Figure 10:
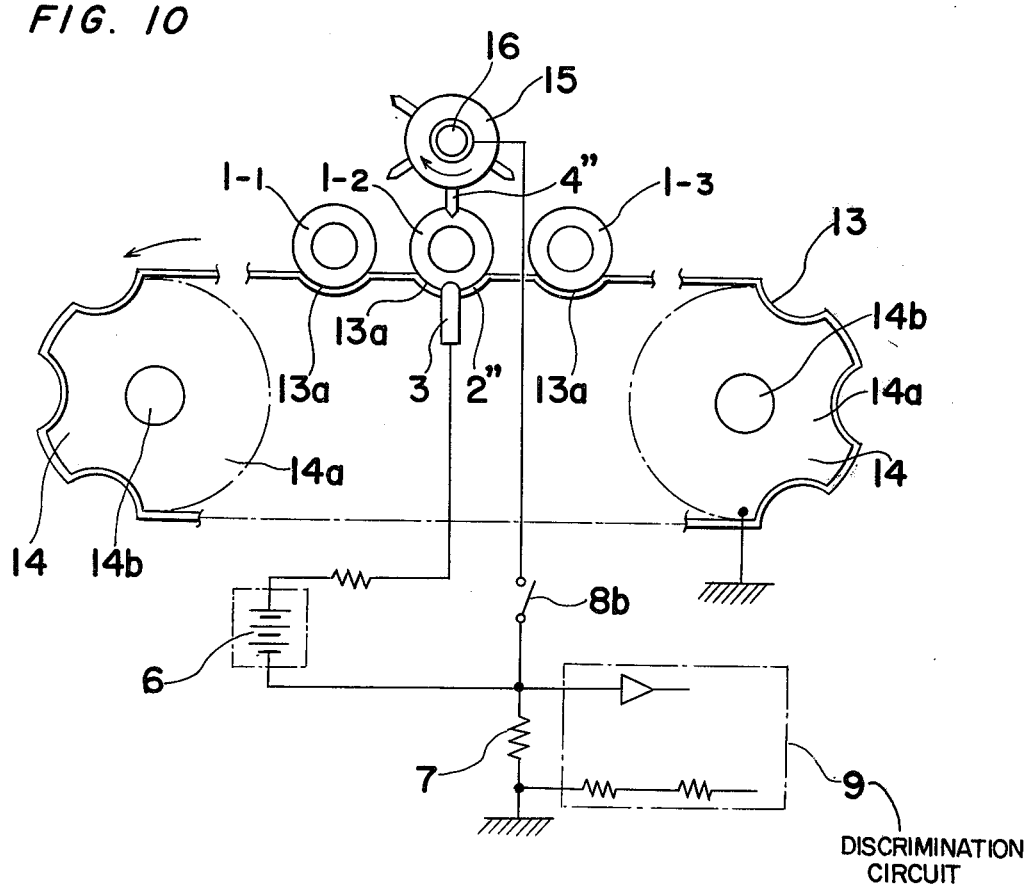

These and other objects and features of the present invention will become apparent from the following description taken in conjunction with the preferred embodiment thereof with reference to the attached drawings, in which;

FIG. 1 is a schematic electrical diagram showing construction of a defect inspection apparatus according to one preferred embodiment of the present invention, FIG. 2 is an electrical diagram showing an equivalent circuit for the apparatus of FIG. 1, FIGS. 3(a) to 3(f) are views similar to FIG. 1, but particularly illustrate the functioning of the apparatus of FIG. 1, FIGS. 4(a) to 4(e) are wave forms of electric currents measured in the apparatus of FIG. 1, FIGS. 5 and 6 are views similar to FIG. 1, but particularly show modifications thereof, FIG. 7 is a views similar to FIG. 1, but particularly shows another modification thereof, FIG. 8 is a diagram showing the characteristics of the vacuum tube employed in the apparatus of FIG. 7, and FIGS. 9 and 10 are views similar to FIG. 1, but particularly show a further modification thereof.

Before the description of the present invention proceeds, it is to be noted that like parts are designated by like reference numerals throughout several views of the accompanying drawings.

Referring now to the drawings, there is schematically shown in FIG. 1 an electrical diagram of the defect inspecting apparatus of the invention in which a body portion $1a$, for example, of an ampoule 1 for injection is placed on a cathode plate 2, while a head or neck portion $1b$ of the ampoule 1 is charged or neutralized through an anode rod 3 and an auxiliary electrode rod 4 is disposed adjacent to the neck portion $1b$. The ampoule 1 is a sealed container of insulating material such as glass containing electrically conductive electrolyte or nonelectrolyte liquid, for example, medicinal fluid 5 and includes the body portion $1a$ of a large internal diameter and the neck portion $1b$ of a reduced internal diameter, both portions $1a$ and $1b$ having approximately the same predetermined thickness. In FIG. 1, the distal end of the neck portion $1b$ is assumed to be the portion to be inspected for the presence of faulty sealed spots such as pin holes, cracks and the like. The anode rod 3 is connected to the plus or positive side of a high voltage DC source 6 having an output in the region from 0.1 to 10 kilovolts (KV) or preferably in the region from 1 to 5 kilovolts (KV) per mm in the distance between the tip of the anode rod 3 and the tip of the auxiliary electrode rod 4. The cathode plate 2 and the auxiliary rod 4 are connected to the minus or negative side of the same high voltage DC source 6 respectively through a measuring resistance 7 and a switch 8 as shown. The cathode plate 2 is a flat plate electrode, for example, of circular configuration which contacts the body portion $1a$ of the ampoule 1 through a large area, and is adapted to be held in contact with the ampoule 1 approximately over the entire surface of the plate 2 during the testing for obtaining sufficient electrical charge in the ampoule 1. The the anode rod 3 is a needle-shaped electrode having a pointed tip, and is disposed adjacent to the neck portion $1b$ of the ampoule 1, with the pointed tip of the rod 3 being spaced a predetermined distance from the distal end of the neck portion $1b$ of the ampoule 1, for example, a distance of 2 mm therefrom on the assumption that output of the DC high voltage source 6 is, for example, in the region from 20 to 24 KV, so that the neck portion $1b$ is charged through electric field of the DC high voltage at the anode rod 3, although sparking-over such as arc distance, spark discharge or the like is not normally produced between the anode rod 3 and the neck portion $1b$. The auxiliary electrode rod 4 is also a needle-shaped electrode having a tip pointed in the similar manner as the anode rod 3 and is disposed adjacent to the neck portion $1b$ of the ampoule 1 with the tip being spaced a predetermined distance, for example, 1 mm from the neck portion $1b$, while a predetermined space, for example, a space of 10 mm is provided between the tip of the auxiliary electrode rod 4 and that of the anode rod 3. Thus, when the auxiliary electrode rod 4 is electrically floating so as to be independent in terms of potential, with the switch 8 being turned off, neither electrical discharging nor charging takes place, but if the switch 8 is turned on to connect the auxiliary electrode rod 4 to the minus side of the high DC voltage source 6, a spark discharge occurs between the auxiliary electrode 4 and the anode rod 3 which simultaneously causes the electrical charge at the neck portion $1b$ of the ampoule 1 to be discharged. The switch 8 of the on-off type for change-over of connection and disconnection between the auxiliary electrode rod 4 and the high voltage DC source 6 should have sufficient capacity to withstand the high voltage of the high DC voltage source 6. Meanwhile, a discriminator 9 is connected to opposite ends of the resistor 7 which is inserted between the cathode plate 2 and the minus side of the high DC voltage source 6 or the ground for detecting the potential developed across the resistor 7 so as to detect the current flowing between the cathode plate 2 and the auxiliary electrode plate 4 as one potential by the discriminator 9. Although not shown in the drawings, the discriminator 9 comprises a reference value setting circuit and an input value comparison circuit or schmidt circuit which emits an output depending on the comparison of the input, for example, with a predetermined reference value.

It should be noted that when the shortest distances between the tip of the anode rod 3 and a detectable fault at the neck portion 1b, between the tip of the anode rod 3 and the tip of the auxiliary electrode rod 4 and between the tip of the auxiliary electrode rod 4 and a detectable fault at the neck portion 1b are represented by $l_1$, $l_2$ and $l_3$ respectively, each of these distance $l_1$, $l_2$ and $l_3$ should be les than 200 mm or preferably in the range from 0.1 to 30 mm or most preferably in the range from 1 to 10 mm.

It should also be noted here that the above detectable fault at the neck portion 1b means a fault which is farthest from the tips of the anode rod 3 and the auxiliary electrode rod 4 and still within the range of detection by the defect inspection apparatus.

The defect inspecting apparatus of the present invention as described above with reference to FIG. 1 may be represented by an equivalent circuit as shown in FIG. 2. In FIG. 2, the ampoule 1 can be regarded as including a first capacitor C1 formed between the outer surface and the inner surface of the neck portion 1b, a resistance R1 formed by the fluid contained in the ampoule 1, and a second capacitor C2 formed between the outer surface and the inner surface of the body portion 1a of the ampoule 1. The charging phenomenon of the anode rod 3 may be regarded as forming a third capacitor C3, the discharging phenomenon as forming a resistance R2, and the neutralizing phenomenon by the auxiliary electrode rod 4 as forming a resistance R3 connected in parallel to the third capacitor C3. Furthermore, in the case where the fluid contained in the ampoule 1 is leaking out of the ampoule through defects therein as mentioned later, this is the equivalent of a leak resistance R4 connected in parallel to the first capacitor C1. The discharge resistance R2, third capacitor C3, first capacitor C1, fluid resistance R1 and second capacitor C2 as described above are sequentially connected in series between the high voltage DC source 6 and the detecting resistance 7.

Referring now to FIGS. 3(a) to 4(e), the method for inspecting the ampoule 1 by employing the defect inspecting apparatus of FIGS. 1 and 2 is described hereinbelow with reference to the cases where the ampoule 1 is free from defects, where a pin hole of more than 2μ is present in the ampoule, where the fluid contained in the ampoule is leaking out through a defect present in the ampoule, and where no fluid is contained in the ampoule.

In FIGS. 3(a), the ampoule 1 is first placed in the inspection position, with the body portion 1a thereof being disposed on the cathode plate 2, and with the neck portion 1b to be tested being positioned between the anode rod 3 and the auxiliary electrode rod 4 in spaced relation to the latter by predetermined distances. By the above arrangement, when the high voltage DC from the high voltage DC source 6 is applied between the anode rod 3 and the cathode plate 2 with the switch 8 turned off, a positive charge is formed at the portion to be tested of the neck portion 1b of the ampoule 1 due to the electric field arising from the high voltage DC of the anode rod 3 as shown, in which case, intermittent spark discharge as shown in FIG. 4(a) is not developed between the anode rod 3 and the ampoule 1. The charging of the ampoule 1 is effected between the glass container and the fluid 5 contained in the glass container, and the potential imparted to the ampoule 1 is increased if sufficient contact area is provided between the body portion 1a and the cathode plate 2. At this time, the auxiliary electrode rod 4 is in an electrically floating state and independent in terms of potential, since the switch 8 is turned off. After the ampoule 1 is charged in the above described manner, when the auxiliary electrode rod 4 is connected to the minus side of the high voltage DC source by turning on the switch 8, a spark discharge is developed between the anode rod 3 and the auxiliary electrode rod 4 for, and simultaneously, since some of electrons ejected from the auxiliary electrode rod 4 by the spark discharge are attracted onto the outer surface of the portion to be tested of the ampoule 1 previously charged, the electrical charge of the ampoule 1 is neutralized between the auxiliary electrode 4 and the portion to be tested at the neck portion 1b of the ampoule 1, with consequent restoration of the ampoule 1 to the original state before the charging. At this time, a neutralizing current $i_1$ is caused to flow from the auxiliary electrode rod 4 to the cathode plate 2, and is detected by the discriminator 9. The neutralizing current $i_1$ normally reaches its maximum value immediately after initiation of the discharge by the auxiliary electrode 4, and subsequently decreases rapidly. In the state as described above, if the ampoule 1 is in the normal condition free from any defects such as pin holes, with a predetermined amount of fluid contained therein, the neutralizing current $i_1$ caused to flow is one unit as shown in FIG. 4(b), while in the case where the ampoule 1 is empty without containing the predetermined amount of fluid therein, the neutralizing current $i_5$ caused to flow is a half unit as shown in FIG. 4(e), since there is no charge stored in the fluid contained in the ampoule 1 as is seen from FIG. 3(f). On the other hand, when the fluid contained in the ampoule 1 is not leaking out onto the surface of the ampoule 1 despite the presence of a defect such as a pin hole larger than 2μ in the ampoule 1, a neutralizing current $i_3$ of more than about two units is caused to flow as shown in FIG. 4(c), but if the same fluid has been leaking out onto the outer surface of the ampoule 1, a spark discharge is continuously developed between the anode rod 3 and the auxiliary electrode rod 4 through the fluid 5 thus leaking out as seen from FIG. 3(e) for causing a discharging current $i_4$ less than about 0.9 unit to flow as shown in FIG. 4(d). Accordingly, if the neutralizing current $i$ as described above is detected by the discriminator 9, it is possible to find out whether the ampoule 1 is normal, or has serious defects such as leakage or absence of the fluid 5 within.

Subsequently, when the auxiliary electrode rod 4 is disconnected from the high voltage DC source 6 by turning off the switch 8 as shown in FIG. 3(c) and becomes independent in terms of potential, the same charge as described with reference to FIG. 3(a) is again built up at the tested portion of the neck portion 1b of the ampoule 1 by the electric field arising from the high voltage DC of the anode rod 3. A charging current $i_2$ as shown in FIG. 4(b) is caused to flow from the cathode plate 2 to the high voltage DC source 6 and detected by the discriminator 9. The charging current $i_2$ reaches a maximum value immediately after initiation of charging of the ampoule 1 and sequentially decreases rapidly. In the normal case where the ampoule 1 is free from such defects as pin holes, and contains a predetermined amount of fluid 5, the charging current $i_2$ caused to flow as shown in FIG. 4(b) approximately equals the previous neutralizing current $i_1$ of one unit. When the ampoule 1 does not contain the predetermined amount of fluid 5 therein, no charging current for the fluid 5 is caused to flow as seen in FIG. 3(f) and therefore, a charging current $i_6$ approximately equal to the previous neutralizing current $i_5$ of a half unit flows as shown in FIG. 4(e). Accordingly, if the condition of the ampoule 1 is classified at the discriminator 9 on the basis of a predetermined low reference value according to the size of the neutralizing current $i_5$ and/or the charging current $i_6$ as described above, it is possible to identify whether the ampoule 1 is normal or empty. Meanwhile, in the case where the fluid contained in the ampoule 1 has not leaked out onto the outer surface of the ampoule 1 despite the presence of a defect such as a pin hole larger than $2\mu$ in the ampoule, the amount of charge of the ampoule 1 is increased due to permeation of the fluid 5 into the defect as is seen from FIG. 3(d) to cause of charging current $i_3$ of more than 2 units to flow. Therefore, by comparing the amount of the above charging current with that of the charge current $i_2$ of a normal ampoule 1 for classification at the discriminator 9, for example, on the basis of fixed reference values having predetermined high figures, it is also possible to detect whether the ampoule 1 is normal or has a pin hole or the like of such an extent as will not allow conspicuous leakage of the fluid 5 therefrom. Furthermore, in the case where the ampoule 1 has a large fault which permits the leakage of the fluid 5 onto the outer surface of the ampoule 1, even if the auxiliary electrode rod 4 is made independent in terms of potential, a spark discharge takes place continuously for some time thereafter in a manner similar to that previously described between the anode rod 3 and the neck portion $1b$ of the ampoule 1 through the fluid 5 leaking out onto the outer surface of the ampoule causing a discharge current $i_4$ of less than about 0.9 unit to continuously flow as shown in FIG. 4(d). Accordingly, by comparing the wave form or the amount of the current of the charge or the discharge of abnormal ampoule 1 with that of the respective charging or discharging current of a normal ampoule 1 for classification at the discriminator 9, for example, on the basis of fixed reference figures or wave forms having predetermined intermediate values, it is possible to find out whether the ampoule 1 is normal or has a defect through which the fluid 5 has leaked.

It should be noted here that, in either of the above described methods of the invention, it is possible to electrically inspect whether the ampoule 1 is normal or not through the inputs to the discriminator 9 developed by turning on and off of the switch 8. More specifically, for example, if predetermined reference values are preset in the discriminator 9 so that an output is developed by the discriminator 9 indicating that the ampoule 1 is normal in the case where the input value is higher than a reference value which differentiates ampoules having less than the predetermined amount of fluid 5 therein, and is simultaneously lower than a reference value which distinguishes the ampoules having a pin hole, and has an integrated value of the input within a predetermined period of time lower than the reference value for differentiating ampoules having their fluid 5 leaking out, acceptable ampoules can be automatically selected in an efficient manner.

In the inspecting methods of the present invention as described above, since the charging of the ampoule 1 and discharging of the auxiliary electrode rod 4 take place readily and positively under stable conditions as compared with the conventional spark discharge method as mentioned earlier, ampoules can be inspected with improved accuracy. Since the current flowing through the ampoule 1 which is sufficient to cause the ampoule to be charged may be of a small value, the disadvantage in the conventional arrangements that the ampoules may be broken by the current flowing therethrough is advantageously eliminated, with a simplification in construction or a reduction in size of the inspecting apparatus on the whole.

The following EXAMPLE is inserted for the purpose of illustrating the present invention, without any intention of limiting the scope thereof.

EXAMPLE

| Container employed for inspection | |
|---|---|
| Ampoule of glass material: | 20 mml type |
| Entire length: | 55 mm |
| Length of neck portion: | 23.5 mm |
| Diameter at neck portion: | 5.1 mm |
| Thickness at neck portion: | 0.3 mm |
| Length of body portion: | 31.5 mm |
| Diameter at body portion: | 12.5 mm |
| Thickness at body portion: | 0.48 mm |

Fluid contained: aqueous glucose solution having an electrical conductivity of 1.50 K$\Omega$/mm Anode rod: The anode rod was disposed at a distance of 1 mm from the neck portion of the ampoule.

Auxiliary electrode rod: The auxiliary electrode rod was disposed immediately below the anode rod at a distance of 10 mm from said anode rod.

Cathode plate: The cathode plate having dimensions of 22 mm × 20 mm was disposed in close contact with the body portion of the ampoule to be inspected.

high voltage DC source: 24 KV

Results of the measurements: A pin hole of $2\mu$ located within 10 mm from the neck portion of the ampoule was detected by an oscillograph at each spark discharge as a signal deflection of approximately three times larger than that in the absence of any pin holes. For confirmation, the pin hole had been preliminarily measured with an optical microscope.

Referring to FIG. 5 showing a modification of the defect inspecting apparatus of FIG. 1, the switch 8 described as connected in series with the auxiliary electrode rod 4 for selectively connecting and disconnecting the electrode rod 4 to and from the negative side of the high voltage DC source 6 in FIG. 1 is dispensed with. The auxiliary electrode rod 4 described in relation to FIG. 1 as disposed in a position adjacent to the neck portion $1b$ of the ampoule 1 is replaced by a similar auxiliary electrode rod $4a$ which is secured, at one end thereof, to a rotatable shaft M1 of driving means, for example, a motor M for pivotal movement of the distal end of the rod $4a$ in the directions shown by the arrows, between a position adjacent to the neck portion $1b$ and a position spaced away from said neck portion $1b$. The cathode plate 2 in FIG. 1 is also replaced by a pair of cathode plates $2a$ and $2b$ which hold the end of the ampoule 1 remote from the neck portion $1b$ therebetween through an increased contact area. By the arrangement described above, since the distal end of the auxiliary electrode rod $4a$ is selectively brought into a position confronting the neck portion 1b and into a position spaced from the same neck portion 1b, an effect similar to the switch 8 in the apparatus of FIG. 1 can be expected.

Referring to FIG. 6, there is shown a further modification of the defect inspecting apparatus of FIG. 1. In the modified defect inspecting apparatus of FIG. 6 which is arranged to simultaneously inspect a plurality of portions of the ampoule 1, the anode rod 3 of needle shape described as employed in the apparatus of FIG. 1 is replaced by a anode plate 3' of flat plate-like configuration. The auxiliary electrode rod 4 and the switch 8 of FIG. 1 are also replaced by auxiliary electrode rods 4'-1, 4'-2 and 4'-3, and switches 8'-1, 8'-2 and 8'-3 respectively. The cathode plate 2 of FIG. 1 being also replaced by a cathode plate 2' having a flat plate-like shape which is held in contact with the bottom surface of the ampoule 1. The edge portion of anode plate 3' confronting the outer surface of the ampoule 1 is formed into a configuration to conform with the external outline of the ampoule 1, with a minimum distance, for example, of 2 mm being provided between the outer surface of the ampoule 1 and the corresponding edge portion of the anode plate 3'. The extreme forward edge of the edge portion of the plate 3' is made thin having a sharp edge pointed toward the outer surface of the ampoule 1 so as to form an apparent needle-shaped electrode with respect to the corresponding auxiliary electrode rods 4'-1 to 4'-3. Each of the auxiliary electrodes 4'-1, 4'-2 and 4'-3 has a pointed extreme end, with the pointed ends thereof being spaced a distance, for example, of 1 mm from the ampoule 1. These pointed ends of the auxiliary electrode rods 4'-1 to 4'-3 are respectively spaced a distance, for example, of 10 mm from the anode plate 3' and positioned to confront the plurality of portions to be tested of the ampoule 1. The switches 8'-1, 8'-2 and 8'-3 of the on-off type are respectively connected in series with the auxiliary electrode rods 4'-1, 4'-2 and 4'-3 for selectively connecting and disconnecting the latter to and from the negative side of the high voltage DC source 6. The cathode plate 2' should preferably be spaced as far as possible from the anode plate 3' and the auxiliary electrode rods 4'-1 to 4'-3, while contacting the ampoule 1 over a large area, for example, approximately the entire bottom surface of the ampoule 1.

By the above arrangement, in the state in which the switches 8'-1 to 8'-3 are all turned off, if any one of the switches 8'-1, 8'-2 and 8'-3 is turned on and off to obtain an output from the discriminator 9, the pressure of the defect in the ampoule 1 at the portion thereof to be tested confronting the auxiliary electrode 4' which is connected to the switch 8' thus turned on and off can be detected in a manner similar to the apparatus of FIG. 1.

The other structures and functions of the defect inspecting apparatus of FIGS. 5 and 6 are similar to those in the apparatus of FIG. 1, and therefore, detailed description thereof is omitted for brevity.

Referring to FIG. 7, there is shown another modification of the defect inspecting apparatus of FIG. 1. In this modification, the switch 8 described as employed in the apparatus of FIG. 1 is replaced by a small switch 8a and a triode 10 capable of withstanding high voltage in a manner as described hereinbelow, and the anode rod 3 is connected to the positive side of the DC high voltage source 6 through a resistor 3a. The high voltage resistant triode 10, for example, a GT tube of 6B54 type has its plate P connected to the auxiliary electrode rod 4 and its grid g to the negative side of a low voltage DC source 12 through the small switch 8a, while its cathode K is connected to the negative side of the high voltage DC source 6, and its heater h is coupled to a DC power source 11. It is to be noted here that the triode 10 is capable of withstanding a high voltage of over 30,000 volts, and its plate current Ip and grid voltage Eg having the relation as in the curve shown in FIG. 8. The plate current Ip is reduced to zero and is not caused to flow, if the grid is coupled, for example, to $-20$ volts at the negative side of the low voltage DC source 12, while sufficient plate current Ip is caused to flow when the grid current Ig is reduced to zero. The change-over of the grid voltage Eg between $-20$ volts and zero is effected by the small switch 8a. More specifically, since the low voltage DC source 12 is connected to the grid of the triode 10 upon turning on of the small switch 8a with consequent suspension of the plate current Ip of the triode 10, the triode 10 is thus in an off state and accordingly, the auxiliary electrode rod 4 is rendered independent of the negative side of the high voltage DC source 6. On the other hand, upon turning off of the small switch 8a, the voltage from the low voltage DC source 12 is prevented from being applied to the grid g of the triode 10, the triode 10 is brought into an on state, and therefore, the auxiliary electrode rod 4 is coupled to the negative side of the high voltage DC source 6 through the triode 10. Accordingly, by rendering the triode 10 operative or inoperative through turning on or off of the switch 8a, the auxiliary electrode rod 4 can be selectively connected to and disconnected from the negative side of the high voltage DC source 6, and thus, the high voltage DC current from the high voltage DC source 6 directed to the auxiliary electrode rod 4 is controlled in flow by the triode 10. The small switch 8a for changing over the triode 10 may have small breakdown voltage, since the switch 8a is only intended to receive and cause to flow the grid voltage Eg which controls the plate current Ip of the triode 10. As is seen from the foregoing description, by employing the triode 10 having a high breakdown voltage, it is possible to use a switch 8a having a small size and a low breakdown voltage for changing over the auxiliary electrode rod 4.

The other structures and functions of the modified defect inspecting apparatus of FIG. 7 are similar to those in the apparatus of FIG. 1, and therefore, detailed description thereof is omitted for brevity.

FIG. 9 illustrates a circuit diagram of a defect inspecting apparatus according to a further modification of the apparatus of FIG. 1, and also to FIG. 10 illustrates one example of an actual circuit arrangement of the modified apparatus shown in FIG. 9. In this modification, the apparatus of FIG. 1 is so modified that the ampoule 1 is automatically transported to a predetermined inspecting position, and subsequently to an unloading position, by a conveyor 13 for intermittently forwarding the ampoules 1 and a driving means 14 for driving the conveyor 13. A plurality of auxiliary electrode rods 4" are radially mounted on a rotary wheel 15, with a motor 16 for driving the rotary wheel 15 being adapted to be turned on or off through a switch 8b. The conveyor 13, for example, of an endless belt type has its surface formed with a series of recesses 13a (FIG. 9) spaced at predetermined intervals for receiving one ampoule in each of the recesses 13a, while one portion of the conveyor 13 is connected to the ground so that the conveyor itself constitutes the cathode plate 2". The anode rod 3 is normally connected to the positive side of the high voltage DC source 6 and the auxiliary electrode rods 4" are normally connected to the negative side of the high voltage DC source 6 through the switch 8b, with the discriminator 9 being coupled between, the conveyor 13 constituting the cathode plate 2" and the negative side of the high voltage DC source 6. The ampoules 1, for example, ampoules 1-1, 1-2 and 1-3 in FIG. 9 are placed one by one into the recesses 13a of the conveyor 13 at one end thereof either automatically or manually, while the conveyor 13 is intermittently moved to the other end by the driving means 14 including, for example, a pair of sprocket wheels 14a supporting the conveyor 13 and suitable drive source (not shown) coupled to one of the shafts 14b of the wheels 14a. When any one of the ampoules 1 thus fed has reached the inspecting position confronting the anode rod 3, the particular ampoule 1 is charged by the action of the anode rod 3 in a manner similar to that described with reference to FIG. 1, and simultaneously inspected for defects upon actuation of the auxiliary electrode rod 4". The ampoule 1 thus tested is further transported to the other end of the conveyor 13 to be sequentially unloaded from the conveyor 13 thereat. Meanwhile, the auxiliary electrode rods 4" are so arranged that a particular one thereof is located at a position having a distance from the ampoule 1 at which no spark discharge takes place between the rod 4" and the anode rod 3 during the initial stage when the particular ampoule 1 to be tested has reached the inspecting position. When the rotary wheel 15 is rotated by the motor 16 upon turning on of the switch 8b, the particular auxiliary electrode rod 4" is brought to a position closer to the anode rod 3 to develop the spark discharge between a rod 4" and the anode rod 3, and is subsequently moved to a position spaced from the ampoule 1 to suspend the spark discharge between the rod 4" and the anode rod 3 for causing the ampoule 1 to be again charged again by the action of the anode rod 3. Accordingly, if the neutralizing current and the discharge current at this time are detected by the discriminator 9 in a manner similar to that of the apparatus of FIG. 1, the ampoules 1 can be automatically inspected successively while the ampoules 1 are transported in the advancing direction according to a series of operations programed in advance.

As is clear from the foregoing description, according to the defect inspection method and apparatus employed therefor of the invention, containers of insulating material, for example, sealed ampoules containing medicinal fluids can be readily inspected for various defects such as pin holes with the use of an inspecting apparatus having a simple construction and operation.

It should be noted here that, although the present invention is mainly described with reference to inspection of ampoules of glass material containing medicinal fluids, the defect inspection method and apparatus employed therefor according to the present invention are not limited in their applications to such ampoules alone, but may be readily applicable to inspection of faulty spots of any containers of insulating material containing electrically conductive electrolyte or nonelectrolyte fluids, such as water, water solutions, distilled water or the like.

Although the present invention has been fully described by way of example with reference to the attached drawings, it is to be noted that various changes and modifications are apparent to those skilled in the art. For example, the polarities of the anode rod and the cathode plate may be reversed depending on the necessity. Therefore, unless such changes and modifications depart from the scope of the present invention, they should be construed as included therein.

What is claimed is:

1. A method of inspecting for defects such as flaws and emptiness in containers of insulating material filled with liquid, which comprises the steps of:
   positioning the container between first and second electrode members;
   holding said first electrode member in contact with a first outer surface portion of the container;
   disposing said second electrode member adjacent to and spaced a predetermined distance from a to be tested second outer surface portion of the container;
   electrically connecting said first and second electrode members to first and second terminals of a high voltage DC source, said DC source applying a voltage of a first polarity to said first electrode member and a voltage of a second polarity, opposite to the first polarity, to said second electrode member for causing the container to store electric energy and for electrically polarizing the contents of the container according to the polarities of the electric charge at the first and second portions of the container;
   detecting the charged electric energy stored in the container; and
   discriminating whether or not the detected energy is within a predetermined range.

2. A method of inspecting for defects as claimed in claim 1, wherein when said detected energy exceeds the predetermined range the presence of the flaws in the container is indicated and, when said detected energy falls below the predetermined range emptiness of the container is indicated.

3. A method of inspecting for defects as claimed in claim 1, wherein said step of detecting is effected during discharge of the electric energy stored in the container, said step of detecting comprising the steps of:
   placing an auxiliary electrode member having applied thereto a voltage of the first polarity from said high voltage DC source at a position in the vicinity of said portion to be tested and also in the vicinity of said second electrode member to establish a spark discharge between said second electrode member and said auxiliary electrode member;
   establishing an electric current, caused by said spark discharge, between said portion to be tested and said auxiliary electrode member through a network formed between said auxiliary electrode member and said first electrode member, for dissipating the stored energy to neutralize the container; and
   detecting the electric current flowing through said network, said current indicative of the electric energy stored in the container.

4. A method of inspecting for defects as claimed in claim 3, wherein the placing of said auxiliary electrode member is effected electrically by closing a switch for electrically connecting said first terminal of said high voltage DC source and said auxiliary electrode member.

5. A method of inspecting for defects as claimed in claim 3, wherein the placing of the auxiliary electrode member is effected by moving said auxiliary electrode member towards the position in the vicinity of said portion to be tested and also in the vicinity of said second electrode member.

6. A method of inspecting for defects as claimed in claim 5, wherein said auxiliary electrode member is mounted on a rotation means and moved to the position in the vicinity of said portion to be tested by rotation of said rotation means.

7. A method of inspecting for defects as claimed in claim 1, wherein said step of detecting is effected during the storing of the electric energy in the container, said step of detecting comprising the steps of:
detecting the electric current flowing through the first electrode member upon supplying of the high voltage DC between the first and second electrode members, said current indicative of the electric energy stored in the container.

8. A method of inspecting for defects as claimed in claim 7, wherein said supplying of the high voltage DC is effected by the steps of:
placing an auxiliary electrode member having applied thereto a voltage of the first polarity from said high voltage DC source at a position in the vicinity of said portion to be tested and also in the vicinity of said second electrode member to establish a spark discharge between said second electrode member and said auxiliary electrode member;
establishing an electric current, caused by said spark discharge, between said portion to be tested and said auxiliary electrode member through a network formed between said auxiliary electrode member and said first electrode member, for dissipating the stored energy to neutralize the container;
removing said auxiliary electrode member from said position for interrupting the spark discharge between said second electrode member and said auxiliary electrode member; and
charging, in response to the absence of the auxiliary electrode member, said portion to be tested by the voltage supplied from the high voltage DC source.

9. A method of inspecting for defects as claimed in claim 8, wherein the placing and removing of the auxiliary electrode member are respectively effected electrically by closing and opening a switching means which electrically connects and disconnects said first terminal of said high voltage DC source and said auxiliary electrode member.

10. A method of inspecting for defects as claimed in claim 8, wherein the placing and removing of the auxiliary electrode member are respectively effected by moving the auxiliary electrode member towards and away from the position in the vicinity of said portion to be tested and also in the vicinity of said second electrode member.

11. A method of inspecting for defects as claimed in claim 10, wherein said auxiliary electrode member is mounted on a rotation means and moved towards and away from the position in the vicinity of said portion to be tested by rotation of said rotation means.

12. A method of inspecting for defects as claimed in claim 3, wherein each of the distances between a tip of said second electrode member and said portion to be tested, between the tip of said second electrode member and a tip of said auxiliary electrode member and between the tip of said auxiliary electrode member and said portion to be tested, are not more than 200 mm.

13. A method of inspecting for defects as claimed in claim 4, wherein the each of distances between the tip of said second electrode member and said portion to be tested, between the tip of said second electrode member and the tip of said auxiliary electrode member and between the tip of said auxiliary electrode member and said portion to be tested are within a range from 0.1 to 30 mm.

14. A method of insepcting for defects as claimed in claim 3, wherein each of the distances between the tip of said second electrode member and said portion to be tested, between the tip of said second electrode member and the tip of said auxiliary electrode member and between the tip of said auxiliary electrode member and said portion to be tested are within a range from 1 to 10 mm.

15. A method of inspecting for defects as claimed in claim 3, wherein the distance between the tip of said auxiliary electrode member and said portion to be tested is 1 mm, and the distance between the tip of said second electrode member and the tip of said auxiliary electrode member is 10 mm.

16. A method of inspecting for defects as claimed in claim 1, wherein said high voltage DC source has a voltage in the range from 0.1 to 10 kilovolts per mm as measured between said second electrode member and said auxiliary electrode member.

17. A method of inspecting for defects as claimed in claim 1, wherein said high voltage DC source has a voltage in the range from 1 to 5 kilovolts per mm as measured between said second electrode member and said auxiliary electrode member.

18. A method of inspecting for defects such as flaws and emptiness in containers of insulating material filled with liquid, which comprises the steps of:
positioning the container between first and second electrode members;
holding said first electrode member in contact with a first outer surface portion of the container;
disposing said second electrode member adjacent to and spaced a predetermined distance from a to be tested second outer surface portion of the container;
electrically connecting said first and second electrode members to first and second terminals of a high voltage DC source, said DC source applying a voltage of a first polarity to said first electrode member and a voltage of a second polarity, opposite to the first polarity, to said second electrode member for causing the container to store electric energy and for electrically polarizing the contents of the container according to the polarities of the electric charge at the first and second portions of the container;
placing an auxiliary electrode member having applied thereto a voltage of the first polarity from said high voltage DC source at a position in the vicinity of said outer surface portion to be tested and also in the vicinity of said second electrode member to establish a spark discharge between said second electrode member and said auxiliary electrode member;
establishing an electric current, caused by said spark discharge, between said portion to be tested and said auxiliary electrode member through a network formed between said auxiliary electrode member and said first electrode member, for dissipating the stored energy to neutralize the container;
detecting the electric current flowing through said network, said current indicative of the electric energy stored in the container; and discriminating whether or not the detected electric current is within a predetermined range.

19. An apparatus for inspecting for defects such as flaws and emptiness in containers of insulating material filled with liquid, said apparatus comprising;

a high voltage DC source for producing a high DC voltage having first and second terminals;

a first electrode member electrically connected to said first terminal of said high voltage DC source, and held in contact with a first outer surface portion of said container;

a second electrode member connected to said second terminal of said high voltage DC source and being disposed to confront a to be tested second outer surface portion of the container at a position spaced a predetermined distance therefrom for causing the high DC voltage supplied to said first and second electrode members to allow the container to store electric energy such that the contents of the container are electrically polarized according to the polarities of electric charge at said first and second portions of the container;

an electric energy detecting means coupled to said first and second electrode members and said high voltage DC source for detecting the charged electric energy stored in the container; and an electric energy discriminating means coupled to said electric energy detecting means for discriminating whether or not the detected energy is within a predetermined range.

20. An apparatus for inspecting for defects as claimed in claim 19, wherein said electric energy discriminating means indicates the presence of the flaws in the container when the detected energy exceeds the predetermined range, and indicates the emptiness of the container when the detected energy falls below the predetermined range.

21. An apparatus for inspecting for defects as claimed in claim 19, wherein said electric energy detecting means comprises:

an auxiliary electrode member connected to said first terminal of said high voltage DC source;

means for selectively placing and removing said auxiliary electrode member at a predetermined position which is in the vicinity of said second portion to be tested and also in the vicinity of said second electrode member to establish, during the presence of said auxiliary electrode member at the predetermined position, a spark discharge between said second electrode member and said auxiliary electrode member and, to interrupt, during the absence of said auxiliary electrode member from the predetermined position, said spark discharge causing an electric current to be developed between said portion to be tested and said auxiliary electrode member through a network, formed between said auxiliary electrode member and said first electrode member, for dissipating the stored energy to neutralize the container;

a current detecting means for detecting the electric current flowing through said network, said current being indicative of the electric energy stored in the container.

22. An apparatus for inspecting for defects as claimed in claim 21, wherein said current detecting means comprises a resistor interposed in said network and a current meter connected in parallel to said resistor.

23. An apparatus for inspecting for defects as claimed in claim 21, wherein said placing and removing means is constituted by a switching means capable of selectively connecting and disconnecting said auxiliary electrode member to and from said high voltage DC source, said auxiliary electrode member being substantially placed at said predetermined position, when said switching means is closed to connect said auxiliary electrode member with said high voltage DC source and, said auxiliary electrode member being substantially removed from said predetermined position when said switching means is opened to disconnect said auxiliary electrode member from said high voltage DC source.

24. An apparatus for inspecting for defects as claimed in claim 23, wherein said switching means is constituted by a vacuum tube means in combination with a switch element.

25. An apparatus for inspecting for defects as claimed in claim 24, wherein said vacuum tube means is triode capable of withstanding high voltage, having a plate connected to said auxiliary electrode rod member and a grid connected to the negative terminal of the high voltage DC source through said switch element and a low voltage DC source, a cathode connected to the negative terminal of the high voltage DC source and a heater coupled to a further voltage source.

26. An apparatus for inspecting for defects as claimed in claim 21, wherein said placing and removing means is a motor member having a rotatable driving shaft, said auxiliary electrode member being secured at one end thereof, for revolving said auxiliary electrode member, during the revolution thereof, said auxiliary electrode member being placed in said predetermined position at one rotated position, and being removed from said predetermined position at other rotated positions.

27. An apparatus for inspecting for defects as claimed in claim 21, wherein said auxiliary electrode member is a plurality of auxiliary electrode rod members and said placing and removing means is a plurality of switch elements corresponding in number to the number of said auxiliary electrode rod members, each of said auxiliary electrode rod members being connectable to said first terminal of said high voltage DC source through a corresponding one of said plurality of switch elements.

28. An apparatus for inspecting for defects as claimed in claim 21, wherein said auxiliary electrode member comprising a wheel member, a plurality of auxiliary electrode rod members each connected to said first terminal of said high voltage DC source and radially extending from said wheel member, and a rotation driving means coupled to said wheel member for rotating said wheel member, whereby said auxiliary electrode rod members are sequentially brought into said predetermined position upon rotation of said wheel member.

29. An apparatus for inspecting for defects as claimed in claim 19, wherein said first and second terminals are negative and positive terminals, respectively.

30. An apparatus for inspecting for defects as claimed in claim 29, wherein said first electrode member is a cathode plate member held in contact with a portion of said container through a large contact area therebetween.

31. An apparatus for inspecting for defects as claimed in claim 29, wherein said first electrode member is a pair of cathode plates holding one portion of said container.

32. An apparatus for inspecting for defects as claimed in claim 29, wherein said first electrode member is a movable conveyor belt member serving as cathode plate member and having recesses formed therein for receiving a plurality of containers for sequentially bringing each of the containers into a testing position facing said second electrode member and said auxiliary electrode member, said movable conveyor belt member being connected to ground.

33. An apparatus for inspecting for defects as claimed in claim 29, wherein said second electrode member is an anode plate member having one edge thereof formed to conform with the outer configuration of the portion to be tested, said anode plate member being connected to the positive terminal of said high voltage DC source.

34. An apparatus for inspecting for defects as claimed in claim 29, wherein said second electrode member is an anode rod member connected to the positive terminal of said high voltage DC source.

35. An apparatus for inspecting for defects as claimed in claim 29, wherein said auxiliary electrode member is an auxiliary electrode rod member connected to the negative terminal of said high voltage DC source.

* * * * *